US00PP33001P3

(12) United States Plant Patent
Hand et al.

(10) Patent No.: US PP33,001 P3
(45) Date of Patent: Apr. 27, 2021

(54) ***CANNABIS* PLANT NAMED 'MR2018001'**

(50) Latin Name: *Cannabis sativa*
Varietal Denomination: MR2018001

(71) Applicant: Aurora Cannabis Enterprises Inc., Edmonton (CA)

(72) Inventors: Andrew Hand, Bradford (CA); Alan Graziano, Toronto (CA)

(73) Assignee: Aurora Cannabis Enterprises Inc., Edmonton (CA)

( * ) Notice: Subject to any disclaimer, the term of this patent is extended or adjusted under 35 U.S.C. 154(b) by 0 days.

(21) Appl. No.: 16/873,049

(22) Filed: Jan. 21, 2020

(65) Prior Publication Data

US 2020/0236829 P1 Jul. 23, 2020

(30) Foreign Application Priority Data

Jan. 18, 2019 (CA) ..... PBR 19-9707

(51) Int. Cl.

| | |
|---|---|
| ***A01H 5/02*** | (2018.01) |
| ***A01H 6/28*** | (2018.01) |
| *A61K 36/185* | (2006.01) |

(52) U.S. Cl.

USPC ..... Plt./258

CPC ..... *A01H 6/28* (2018.05); *A61K 36/185* (2013.01)

(58) Field of Classification Search

USPC ..... Plt./258, 263.1

CPC ... A01H 5/02; A01H 5/00; A01H 5/12; A01H 6/28

See application file for complete search history.

*Primary Examiner* — Kent L Bell

(74) *Attorney, Agent, or Firm* — Christensen O'connor Johnson Kindness PLLC

(57) ABSTRACT

A new cultivar of *Cannabis* plant named 'MR2018001' that is characterized by about 9% THC and 9% CBD by dry weight and microbial resistance.

2 Drawing Sheets

Genus and species: *Cannabis sativa.*
Variety denomination: 'MR2018001'.

CROSS-REFERENCE TO RELATED APPLICATIONS

This application claims the benefit of priority under 35 U.S.C. 199(f) to Canadian Plant Breeders' Rights Application Number 19-9707, which was filed for the instant plant variety on Jan. 18, 2019.

BACKGROUND OF THE INVENTION

The present invention relates to a new and distinct *Cannabis* (*Cannabis sativa*) cultivar designated as 'MR2018001'.

'MR2018001' is a selection resulting from a controlled-cross between the female *Cannabis sativa* variety 'Afghani Hawaiian' (unpatented) and the male *Cannabis sativa* variety 'Jamaican Landrace' (unpatented). The plants were grown at an indoor *Cannabis* facility in Markham, Ontario, Canada. The plants were flowered under standard indoor environment conditions with High Pressure Sodium lamps.

Seeds from the cross were sown in Markham, Ontario, Canada and plants were screened for a number of traits including tetrahydrocannabinol (THC) and cannabidiol (CBD) levels, yield, flowering time, disease resistance and flower morphology. An individual plant having about 9% THC and about 9% CBD by dry weight and exhibiting resistance to microbial growth was chosen to be 'MR2018001'.

In February 2016, 'MR2018001' was first asexually propagated by apical stem cuttings approximately 10 cm long and having multiple auxiliary meristems, in Markham, Ontario, Canada. 'MR2018001' is stable and reproduces true to type in successive generations of asexual reproduction. This cultivar has increased resistance to microbial growth and higher flower yield for enhanced cultivation and production of flower yield and extracts thereof.

BRIEF SUMMARY OF THE INVENTION

This invention relates to a new and distinctive *Cannabis* cultivar designated as 'MR2018001'.

'MR2018001' exhibits about 9% THC and about 9% CBD by dry weight. 'MR2018001' also exhibits resistance to microbial growth.

BRIEF DESCRIPTION OF THE DRAWINGS

The accompanying color photographs depict characteristics of 'MR2018001'. The colors shown are as true as can be reasonably obtained by conventional photographic procedures.

DETAILED BOTANICAL DESCRIPTION

Figure 1:
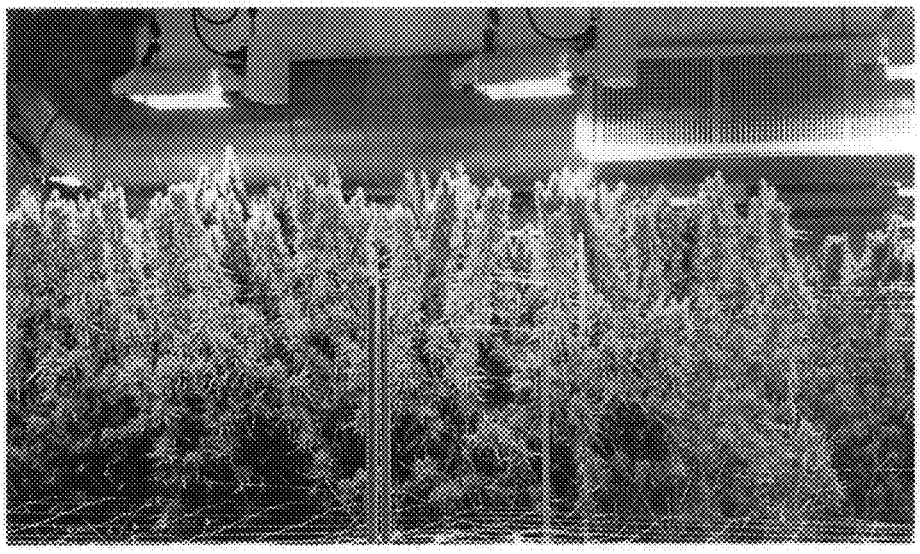
FIG. 1 shows multiple, whole plant clones of 'MR2018001'.
Figure 2:
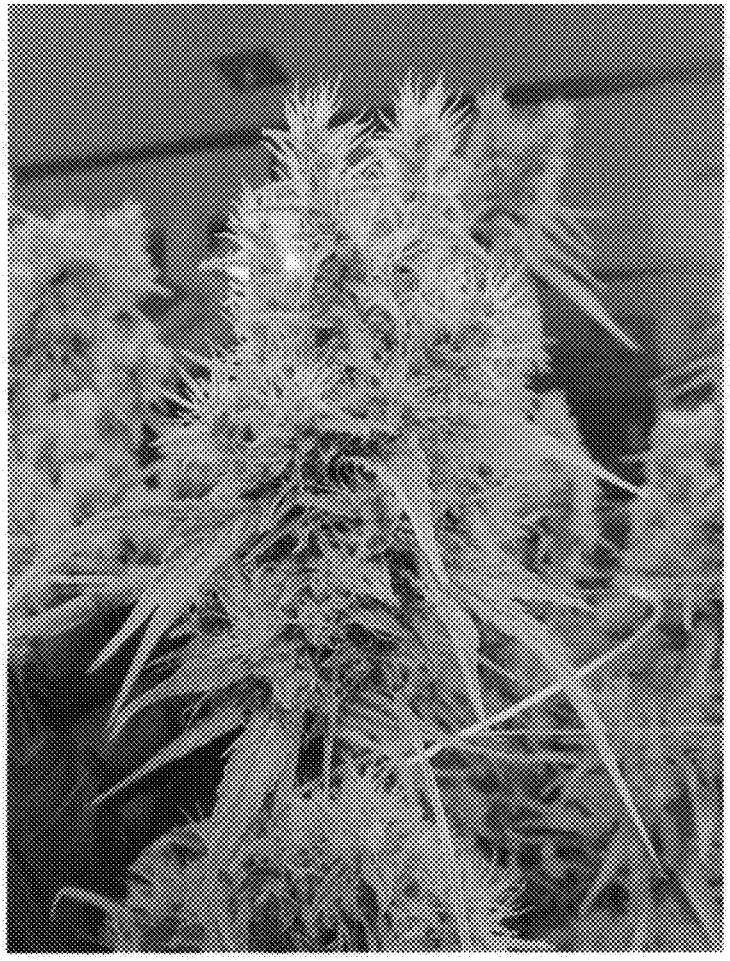
FIG. 2 shows a close-up view of an inflorescence and foliage of 'MR2018001'.

The following is a detailed description of the new cultivar 'MR2018001'.

'MR2018001' has not been tested under all possible environmental conditions. Phenotypic differences may be observed with variations in environment without any variance in genotype.

The traits of 'MR2018001' have been repeatedly observed and represent the distinguishing characteristics of 'MR2018001'.

The data that follows was collected in Markham, Ontario Canada.

Plants were flowered under standard indoor environmental conditions with High Pressure Sodium lamps. Clones were cut from healthy mothers and allowed to root for 14 to 18 days prior to being introduced to the flower room. The room was maintained at 18 hour days/6 hour nights for a week to allow the cuttings to establish adequate vegetative tissue. The floral transition was initiated by switching to 12 hour days and 12 hour nights. Flowering lasted 8-9 weeks before harvest, at which point samples were taken for chemical analysis, and yield was quantified. Morphological measurements were taken from plants aged 9 weeks post-floral transition.

Standard in-house developed nutrients were used throughout growth, and the plants were defoliated and pruned as necessary throughout the cycle.

In the following description, the color determination is in accordance with the 2017 Munsell Plant Tissue Color Book, except where general color terms of ordinary dictionary significance are used.

Classification:

*Denomination*.—'MR2018001'.

*Family*.—Cannabacaeae.

*Genus*.—*Cannabis*.

*Species*.—*Cannabis sativa*.

*Common name*.—Marijuana.

Parentage: Female *Cannabis sativa* variety 'Afghani Hawaiian' and male *Cannabis sativa* variety 'Jamaican Landrace'.

Propagation: 'MR2018001' is asexually (clonally) propagated from vegetative cuttings. It takes approximately 14-18 days to produce a rooted young plant. Roots are fine and well-branched.

Plant:

*Height*.—120 cm-135 cm.

*Diameter*.—35 cm-60 cm.

Stems:

*Length/height*.—110 cm-130 cm.

*Width/diameter*.—7 mm-11 mm.

*Color*.—2.5 GY 7/8, 5 RP 3/4.

*Shape*.—Tubular.

*Texture*.—Fibrous and Pubescent.

*Lateral branch length*.—15 cm-35 cm.

Foliage:

*Type/form*.—Palmately Compound.

*Arrangement*.—Alternate.

*Attachment*.—Petiolate.

*Leaf width*.—9 cm.

*Leaf length*.—10 cm.

*Number of leaflets per leaf*.—5-7.

*Leaflet shape*.—Lanceolate.

*Leaflet length*.—3 cm-10 cm.

*Leaflet width*.—0.4 cm-1.5 cm.

*Leaflet margin*.—Serrate.

*Leaflet apex*.—Acuminate.

*Leaflet base*.—Attenuate.

*Leaflet color, upper surface*.—7.5 GY 3/4.

*Leaflet color, lower surface*.—5 GY 6/4.

*Venation pattern and description, upper and lower leaflet surfaces*.—Pinnate.

*Texture (both surfaces)*.—Pubescent, primarily on the abaxial side and along leaf vasculature.

*Stipules*.—Present, 2 per node on either side of a petiole, attenuated.

*Leaf fragrance*.—Earthy, aromatic, herbal aroma.

Petiole:

*Length*.—2.5 cm.

*Diameter*.—0.25 cm.

*Texture*.—Fine, short non-glandular trichomes.

*Color*.—2.5 GY 5/6 (Munsell).

Inflorescence: The plant is a genetically female dioicous plant and, therefore, produces predominantly female flowers. There are no male-only plants. There is a very low incidence of hermaphroditism.

*Blooming habit*.—Short day photoperiod sensitive.

*Attachment*.—Subsessile.

*Bracts*.—Covered with trichomes and resin glands with 2 stigmas emerging.

*Bract color*.—5GY 7/8 (Munsell) (typical and observed).

*Trichomes*.—Capitate-sessile, capitate-stalked, bulbous, and non-glandular (cystolith hairs); trichomes are present on almost all aerial organs but are present at highest concentration on female flowers (calyxes, bracts, etc.) as well as subtending intra-flower leaves.

*Bract trichome and resin gland color*.—Trichomes are clear, and will turn amber (approximately 10R 4/10 (Munsell)) during senescence.

*Inflorescence color*.—7.5 GY 5/6, 5 GY 4/8 (Munsell).

*Number of inflorescences per plant*.—80-130.

*Diameter*.—4 cm-10 cm.

*Length*.—3 cm-18 cm.

*Inflorescence anthocyanin*.—Absent for both female and male (very rare) flowers.

*Inflorescence thc content*.—About 9%.

*Blooming period*.—Average flowering length of 61.8 days (of 36 production batches). Male flowering: male flowers are very rare; if present, typically develop between week 2 and 4 of general flowering.

*Inflorescence fragrance*.—earthy, aromatic, herbal aroma.

Reproductive organs:

*Pistils*.—1.

*Quantity (of stigmas) per flower*.—2.

*Stigma length*.—1.2 cm.

*Stigma width*.—0.66 mm.

*Stigma color*.—5 Y 8/2, 10 R 4/8 (Munsell).

THC and CBD content (quantified with a Waters LC-MS/MS, running an Acetonitrile:Methanol:2-propanol gradient mobile phase through a Raptor ACR-18, 2.7 um, 2.1×150 mm column):

*Average % thc by dry weight*.—about 9%.

*Average % cbd by dry weight*.—about 9%.

Yield:

*Average flower yield*.—833 g/m$^2$ (grams dried, trimmed flower per m$^2$ of growing space, which includes optimal cultivation density).

*Average trim yield.*—425 g/m$^2$ (grams trichome rich leaf material per m$^2$ growing space that is removed during harvest/trimming).

Disease and insect/pest resistance: 'MR2018001' exhibits resistance to aerobic bacteria, yeast, mold and coliform bacteria as shown in Table 1.

TABLE 1

'MR2018001' resistance to aerobic bacteria, yeast, mold and coliform bacteria.

| | |
|---|---|
| Average Aerobic Bacteria Count (per plant, in colony forming units (CFUs)) | 268.6 |
| Average Yeast and Mold Count (per plant, in CFUs) | 368 |
| Average coliform bacteria count (per plant, in CFUs) | 46 |

COMPARISON WITH PARENTAL LINES AND KNOWN VARIETY

'MR2018001' may be compared with its parental lines with respect to THC and CBD content. Using Waters LC-MS/MS, running an Acetonitrile:Methanol:2-propanol gradient mobile phase through a Raptor ACR-18, 2.7 um, 2.1×150 mm column to quantify THC and CBD, 'MR2018001' exhibits about 9% THC by dry weight, the female parent exhibits 20% THC by dry weight and the male parent exhibits 2% THC by dry weight. In addition, 'MR2018001' exhibits about 9% CBD by dry weight, the female parent exhibits 0% CBD by dry weight and the male parent exhibits 4% CBD by dry weight.

A close variety of *Cannabis* known to the inventors is the commercial variety 'Girl Scout Cookies'. Variety 'MR2018001' can be distinguished from the variety 'Girl Scout Cookies' by its increased resistance to microbial growth, as shown in Table 2.

TABLE 2

Comparison between 'MR2018001' and 'Girl Scout Cookies': Microbial resistance

| Variety | # of Cycles Grown | Average Aerobic Bacteria Count* | Average Yeast and Mold Count** | Average Coliform Bacteria Count* |
|---|---|---|---|---|
| 'MR2018001' | 5 | 268.6 | 368 | 46 |
| 'Girl Scout Cookies' | 15 | 59270 | 52450 | 760 |

**Aerobic Bacteria Count, Yeast and Mold Count and Coliform Bacteria Count were determined per plant, in colony forming units (CFUs).

Variety 'MR2018001' can also be distinguished from the variety 'Girl Scout Cookies' with respect to the morphological traits listed in Table 3. In particular, 'MR2018001' is a tall cultivar with short intranodes. As a result, the number of flowers produced on each plant is high, which translates to a high yield of dry flower per plant.

TABLE 3

Comparison between 'MR2018001' and 'Girl Scout Cookies': Morphological traits

| Characteristic | 'MR2018001' | 'Girl Scout Cookies' |
|---|---|---|
| Overage Average Height | 111.6 cm | 69.6 cm |
| Average Height | 123.6 cm | 74 cm |
| Average # of Nodes | 32.7 | 22.3 |
| Average Internodal Length | 6.6 cm | 6.6 cm |
| Average Flower Width | 4.4 cm | 5.3 cm |
| Grams of flower per plant | 23.0 | 19.0 |

The invention claimed is:

1. A new and distinct cultivar of *Cannabis* plant named 'MR2018001' as described and illustrated herein.

* * * * *